United States Patent
Loescher

(10) Patent No.: US 6,725,858 B2
(45) Date of Patent: Apr. 27, 2004

(54) VALVED AEROSOL TEE ADAPTER ASSEMBLY

(75) Inventor: Thomas C. Loescher, Rancho Santa Fe, CA (US)

(73) Assignee: Hudson Respiratory Care Inc., Temecula, CA (US)

( * ) Notice: Subject to any disclaimer, the term of this patent is extended or adjusted under 35 U.S.C. 154(b) by 180 days.

(21) Appl. No.: 09/850,870

(22) Filed: May 7, 2001

(65) Prior Publication Data

US 2002/0162554 A1 Nov. 7, 2002

(51) Int. Cl.[7] .............................................. A61M 11/00
(52) U.S. Cl. ........................... 128/200.14; 128/202.27; 128/205.24; 128/912
(58) Field of Search ................. 128/200.14, 200.21, 128/200.22, 200.16, 912, 202.27, 205.24

(56) References Cited

U.S. PATENT DOCUMENTS

| | | | |
|---|---|---|---|
| 3,724,489 A | 4/1973 | Eross | |
| 4,044,793 A | * 8/1977 | Krueger et al. ............. | 137/881 |
| 4,231,361 A | 11/1980 | Wise | |
| 4,454,877 A | 6/1984 | Miller et al. | |
| 4,506,665 A | * 3/1985 | Andrews et al. ....... | 128/202.27 |
| 4,510,933 A | 4/1985 | Wendt et al. ............... | 128/207 |
| 4,592,349 A | 6/1986 | Bird | |
| 4,951,661 A | 8/1990 | Sladek | |
| 5,165,398 A | 11/1992 | Bird | |
| 5,385,141 A | * 1/1995 | Granatiero ............. | 128/201.19 |
| 5,396,883 A | * 3/1995 | Knupp et al. .......... | 128/200.14 |
| 5,653,223 A | * 8/1997 | Pruitt .................... | 128/200.21 |
| 5,662,100 A | * 9/1997 | Fox et al. .............. | 128/205.24 |
| 5,687,912 A | * 11/1997 | Denyer ....................... | 239/343 |
| 5,738,088 A | 4/1998 | Townsend | |
| 5,813,401 A | * 9/1998 | Radcliff et al. ........ | 128/205.24 |
| 6,044,841 A | 4/2000 | Verdun et al. | |
| 6,102,038 A | * 8/2000 | DeVries ................. | 128/205.24 |
| 6,135,108 A | 10/2000 | Hoenig ........................ | 128/205 |
| 6,450,163 B1 | * 9/2002 | Blacker et al. ......... | 128/200.18 |

* cited by examiner

*Primary Examiner*—Weilun Lo
*Assistant Examiner*—Darwin P Erezo
(74) *Attorney, Agent, or Firm*—Knobbe, Martens, Olson & Bear, LLP

(57) ABSTRACT

A valved aerosol Tee adapter assembly comprises a housing member having an upper section with a first interior passageway, a spring chamber between the first passageway and the inner wall of said upper section and a valve seat formed along the upper edge of said upper section, and a lower section having a second passageway contiguous with the first passageway, a compressible spring positioned in the chamber; and a valve reciprocally movable in the housing comprising a valve actuator slidably received in the second passageway having an upper surface for engaging the compressible spring, and a valve member secured to the valve actuator.

15 Claims, 3 Drawing Sheets

VALVED AEROSOL TEE ADAPTER ASSEMBLY

BACKGROUND OF THE INVENTION

Figure 1:
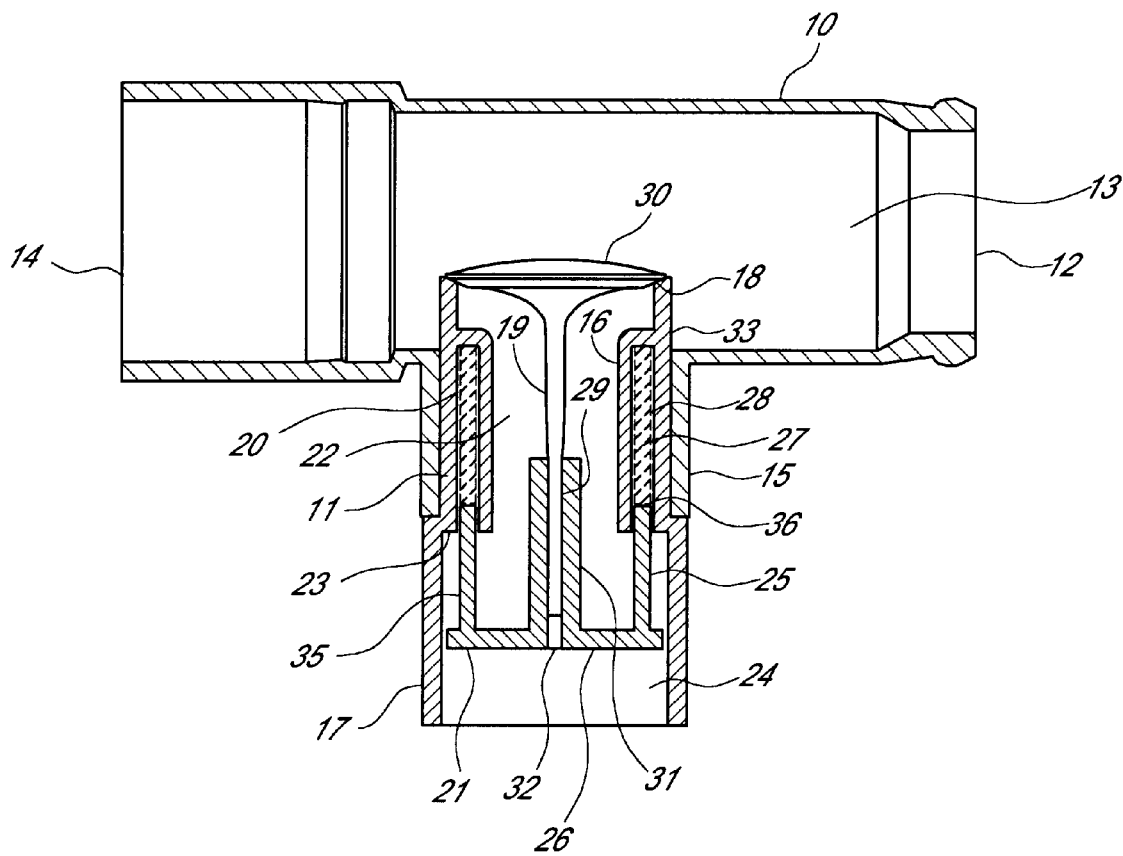
Figure 2:
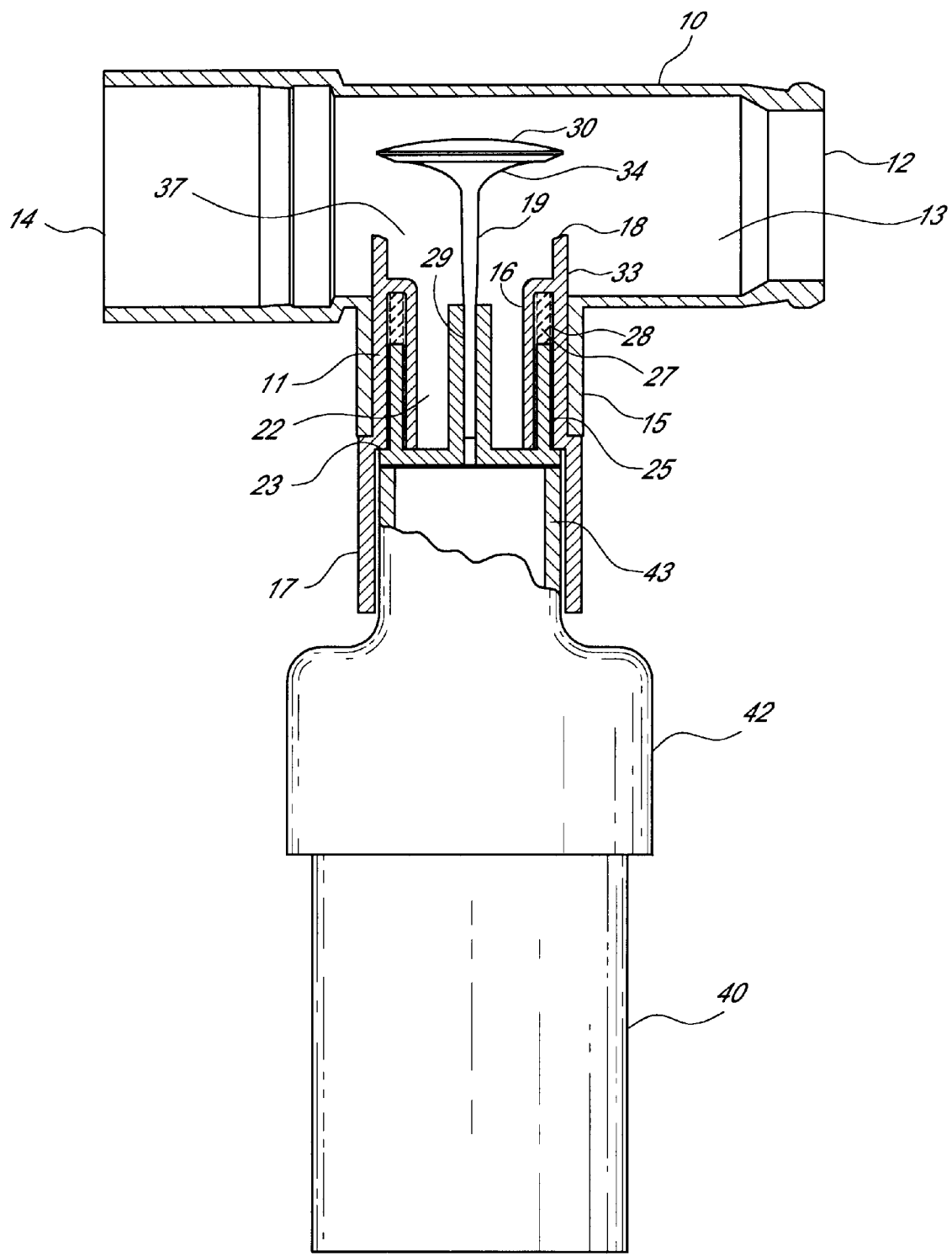
Figure 3:
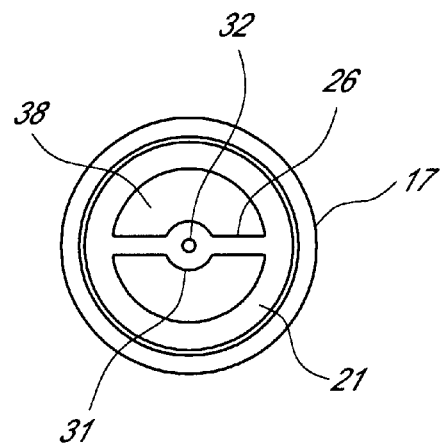
Figure 4:
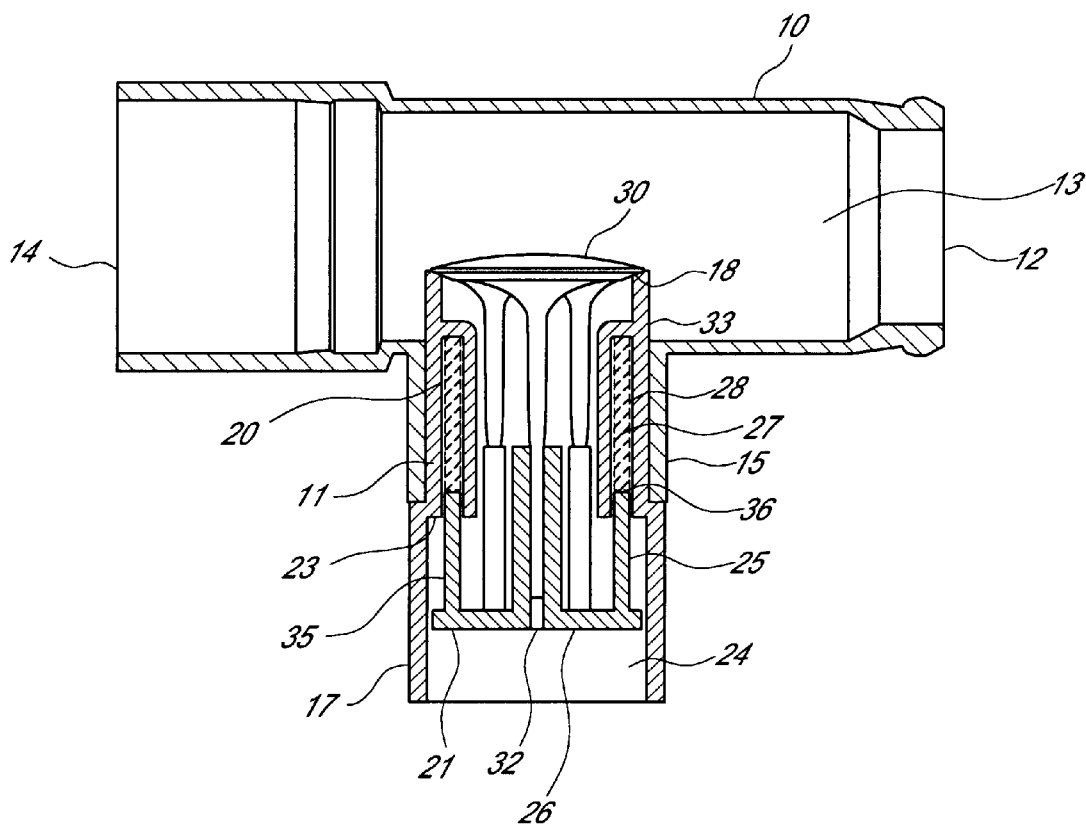

In respiratory therapy, treatment with an aerosol directed to the patent via a ventilator circuit is often prescribed. For such practice, a nebulizer is attached to a side port of a Tee connector in the ventilator circuit. Ventilation is temporarily interrupted while the Tee connector and nebulizer are attached to and removed from the circuit. Moreover, opening the respiratory circuit to atmosphere results in exposure of other patients and attending personnel to bacteria, fluids, etc. from the patient present in the circuit. During the aerosol treatment, fluid in the Tee connector from condensation or from the nebulized aerosol particles may drain back into the nebulizer, thereby contaminating the medicament fluid to be nebulized.

A quick-connect adapter valve for connecting a nebulizer to a respiratory circuit is disclosed in U.S. Pat. No. 4,951,661. Although the apparatus allows the respiratory circuit to remain closed and without interrupting ventilation when connecting a nebulizer for aerosol treatment, the device has some disadvantageous structural components and features. The present invention is directed to an apparatus which provides for securing a nebulizer in a respiratory circuit without interrupting ventilation and for sealing the circuit when the nebulizer is removed. The apparatus of the invention incorporates structures and features which avoid the disadvantages of the device described in the aforesaid patent.

SUMMARY OF THE INVENTION

The present invention is directed to a valved aerosol Tee adapter assembly for removably securing a nebulizer in a Tee connector used in a respiratory circuit. The device features a structure in which the valve spring is housed without exposure to or interference with the aerosol generated from the nebulizer. The structure also provides a substantially unobstructed channel for nebulized particles to pass into the Tee connector. The device includes a wall extending into the Tee connector passageway for preventing fluids and condensate from draining back into the nebulizer. These as well as other advantages and components of the assembly of the invention will be described in detail hereinafter.

BRIEF DESCRIPTION OF THE DRAWINGS

FIG. 1 is a sectional elevational view of the adapter assembly of the invention in a closed condition secured in a Tee connector;

FIG. 2 is a sectional elevation of the adapter assembly in an open condition in the Tee connector.

FIG. 3 is a plan view of the lower end of the adapter assembly of the invention; and FIG. 4 is an elevational view of the adapter assembly showing a plurality of support members for securing the valve member to the actuator.

DETAILED DESCRIPTION OF THE PREFERRED EMBODIMENTS

FIGS. 1 and 2 illustrate the valved adapter assembly of the invention installed in a Tee connector 10. The Tee connector has inlet port 12 and outlet port 14 and interior passageway 13. The inlet and outlet ports are connected to ventilator breathing circuit hoses for supplying inspiratory gas from a ventilator or respirator to a patient. The valved assembly includes a housing having an upper section 11 and a lower section 17. In the preferred embodiment illustrated, the housing is substantially cylindrical with upper cylindrical section 11 having a smaller diameter than the cylindrical lower section 17. A cylindrical upper section allows the housing to be inserted with a gas sealing force-fit into the side port 15 of the Tee connector 10. A wall 16 is formed interiorly of the upper housing section 11. The space between wall 16 and inner wall surface 20 of upper section 11 forms the annular chamber 27 for housing a spring 28.

As shown in FIG. 1, valve 30 forms a gas seal against valve seat 18 along the upper edge of upper housing section 11. Valve actuator 25 comprises annular wall 35 extending from actuator ring 21. The upper edge 36 of annular wall 35 engages spring 28 which is biased in an expanded condition to close the valve. The valve actuator includes a valve support collar 31 into which a valve support member is positioned. In the embodiment illustrated, the valve support member includes a rod 19 integrally formed and extending downwardly from valve 30 and a lower rod portion 29 secured into channel 32 within collar 31. Preferably, the lower portion of rod 19 is tapered for a force-fit within channel 32. However, other features, shapes or components of the valve support member may be used for securing the valve to the valve actuator 25. The valve support collar 31 is integrally formed with the valve actuator and supported by ribs 26 extending between the collar and the valve actuator ring 21. By separately forming or molding the valve actuator and valve components, manufacture and assembly of the device is enhanced.

As shown in FIG. 2, a nebulizer 40 inserted in the lower section 17 of the housing urges the valve actuator and valve upperwardly from the closed position shown in FIG. 1 to the open position of FIG. 2. FIG. 2 illustrates the valve assembly of the invention in an open condition with valve actuator 25 moved upwardly in lower passageway 24 by urging aerosol outlet pipe 43 of nebulizer lid 42 into the passageway. The upper edge of outlet pipe 43 is forced against actuator ring 21 whereby continued upward pressure of the nebulizer forces the biased valve actuator to open the valve. The shoulder 23 forms a stop for upward movement of the valve actuator within lower passageway 24. With the valve actuator urged against shoulder 23 spring 28 is compressed and valve 30 is moved away from valve seat 18 so that upper passageway 22 within the upper section 11 of the valve housing communicates with the interior passageway 13 of the Tee connector 10. With the valve open, there is an unobstructed channel 37 between upper passageway 22 and the interior passageway 13 of the Tee connector for passage of aerosol from a nebulizer via aerosol outlet pipe 43 into the Tee connector. Aerosol from the nebulizer is directed through openings 38 in the valve actuator (see FIG. 3), along upper passageway 22 and unobstructed channel 37 into the Tee connector. The underside surface 34 of valve 30 is preferably arched or tapered to form a surface for better dispersing the aerosol uniformly within interior passageway 13 of the Tee connector. Preferably, the upper surface of the valve member is convex, as shown, to prevent pooling of condensate on the valve.

Preferably, the interior diameter of the lower passageway 24 provides a convenient force-fit with the aerosol outlet pipe of a nebulizer. This, lower passageway of the adapter assembly should be of a size so that the nebulizer may be easily attached and removed by hand. With the valved adapter assembly and Tee connector installed in a respiratory circuit, patient ventilation may be carried out normally without opening the circuit, or interrupting ventilation when a nebulizer is to be attached for administering aerosol treatment. Thereafter, the nebulizer is removed, again without interrupting patient ventilation. Examples of suitable nebulizers shown and described in U.S. Pat. Nos. 4,588,129 and Re. 33,642

An advantage of the device of the invention is that spring 28 does not obstruct the aerosol passageways, nor is it exposed to the aerosol thereby avoiding aerosol condensation on the spring and deterioration of the spring due to exposure to the aerosol. Another advantage of the device of the invention is that the upper section 11 of the housing extends into passageway 13 forming a barrier to prevent liquid from draining from the interior of the Tee connector into the nebulizer. Such a feature is shown with upper section wall 33 extending into the passageway 13 of the Tee connector 10 to form the liquid barrier. These and other advantages will be evident to those skilled in the art.

What is claimed is:

1. A valved aerosol Tee adapter assembly for directing aerosol from a nebulizer therethrough comprising:

- a housing member comprising a cylindrical outer wall and a cylindrical inner wall and a passageway interiorly of said inner wall for directing aerosol therethrough;
- an enclosed annular chamber formed between said inner wall and said outer wall, and a valve seat formed along an upper edge of said housing member;
- a spring positioned in said enclosed annular chamber; and
- a valve reciprocally movable in said housing comprising a valve actuator having an annular wall slidably received in said enclosed annular chamber and having an upper surface for engaging said spring, whereby said annular wall, said inner wall and said outer wall cooperate to substantially isolate said enclosed annular chamber from said passageway and whereby said spring therein is substantially unexposed to aerosol from said passageway, and a valve member secured to said valve actuator.

2. An assembly of claim 1 including one or more support members for securing said valve to said valve actuator.

3. An assembly of claim 2 wherein said valve member comprises a valve for sealingly engaging said valve and has a curved lower surface portion exposed in said passageway.

4. An assembly of claim 3 including a single support member extending from the center of the lower surface of said valve member and secured to said valve actuator.

5. An assembly of claim 4 wherein said single support member is removably secured to said valve actuator.

6. An assembly of claim 5 wherein said valve actuator includes a collar having a channel therein for receiving said single support member.

7. An assembly of claim 4 wherein said support member comprises a rod.

8. An assembly of claim 7 wherein said rod is integrally formed with said valve member.

9. An assembly of claim 1, 3, 4, 5, 6, 7 or 8 wherein said spring is biased to urge said valve in sealing engagement with said valve seat.

10. In combination an adapter assembly of claim 9 and a Tee connector having a side port and cylindrical fitting communicating with the interior connector passageway said adapter assembly secured into said fitting whereby a portion of the cylindrical outer wall of the housing member extends into the connector passageway to form a circular wall therein.

11. In combination an adapter assembly of claim 9 and a Tee connector having an interior passageway for the flow of gas there through and a side port and cylindrical fitting communicating with the interior Tee connector passageway, said adapter assembly secured into said fitting whereby part of the housing extends into the connector passageway to form a wall therein, and a nebulizer secured in said adapter assembly against said valve actuator whereby said valve actuator is moved in said passageway and said valve member is spaced apart from said valve seat whereby said passageway is open to the interior Tee connector passageway.

12. An assembly of claim 1 wherein said assembly is operable between a closed condition with said spring biased in an expanded condition in said chamber and urging said valve actuator to close said valve, and an open condition wherein said valve actuator is forced against said spring and compresses said spring sufficiently to move said valve actuator to open said valve.

13. In combination an adapter assembly of claim 12 and a Tee connector having an interior passageway for the flow of gas therethrough and a side port communicating with said interior passageway, and wherein, in an assembled condition with said housing member secured in said side port, said housing member extends into said interior passageway sufficiently to form a liquid barrier therein capable of preventing flow of liquid from said Tee connector into said adapter assembly when said valve is open.

14. An assembly of claim 13 including one or more support members for securing said valve member to said actuator.

15. An assembly of claim 13 wherein said outer wall of said housing member extends into said interior passageway to form a walled liquid barrier therein.

* * * * *